US010040746B2

(12) United States Patent
Kon et al.

(10) Patent No.: US 10,040,746 B2
(45) Date of Patent: *Aug. 7, 2018

(54) CARBOXYLIC ACID RECOVERY FROM MAGNESIUM CARBOXYLATE MIXTURE

(71) Applicant: PURAC BIOCHEM BV, Gorinchem (NL)

(72) Inventors: Adriaan Dirk Kon, Meerkerk (NL); André Banier De Haan, Best (NL); Paulus Loduvicus Johannes Van Der Weide, Breda (NL); Tanja Đekic Živkovic, Den Bosch (NL); Lucien Henri Leander Jozef De Koninck, Dongen (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,586

(22) Filed: Jul. 14, 2016

(65) Prior Publication Data
US 2016/0318837 A1 Nov. 3, 2016

Related U.S. Application Data

(63) Continuation of application No. 14/402,441, filed as application No. PCT/EP2013/060594 on May 23, 2013, now Pat. No. 9,422,217.

(60) Provisional application No. 61/651,040, filed on May 24, 2012.

(30) Foreign Application Priority Data

May 24, 2012 (EP) ..................... 12169359

(51) Int. Cl.
| C07C 51/42 | (2006.01) |
| C07C 51/02 | (2006.01) |
| C01F 5/10 | (2006.01) |
| C01F 5/02 | (2006.01) |
| C01F 5/16 | (2006.01) |
| C01B 7/03 | (2006.01) |
| C01F 5/30 | (2006.01) |
| B01J 39/05 | (2017.01) |
| B01J 49/53 | (2017.01) |

(52) U.S. Cl.
CPC .............. *C07C 51/02* (2013.01); *B01J 39/05* (2017.01); *B01J 49/53* (2017.01); *C01B 7/035* (2013.01); *C01F 5/02* (2013.01); *C01F 5/10* (2013.01); *C01F 5/16* (2013.01); *C01F 5/30* (2013.01)

(58) Field of Classification Search
CPC ....... C07C 51/02; C07C 53/122; C07C 55/10; C07C 55/14; C07C 57/04; C07C 57/145; C07C 57/15; C07C 59/01; C07C 59/08; C07C 59/265; C07C 63/26; B01J 39/043; B01J 49/0069; C01B 7/035; C01F 5/00; C01F 5/10; C01F 5/16; C01F 5/302
See application file for complete search history.

(56) References Cited

U.S. PATENT DOCUMENTS

| 3,694,153 A * | 9/1972 | Williams | C01B 25/237 423/112 |
| 4,661,258 A * | 4/1987 | Phillips | B01J 47/10 210/189 |
| 5,167,939 A * | 12/1992 | Lohrberg | C01D 3/145 423/155 |
| 5,279,716 A * | 1/1994 | Sharma | C25C 3/04 205/404 |
| 5,858,119 A * | 1/1999 | Mayne | B01J 49/0078 134/19 |
| 2006/0276674 A1 * | 12/2006 | Kushiku | C07C 51/47 562/562 |
| 2011/0098438 A1 | 4/2011 | Okamoto | |
| 2012/0259138 A1 * | 10/2012 | Dunuwila | C07C 51/02 562/590 |

FOREIGN PATENT DOCUMENTS

| DE | 2748133 | * 3/1979 |
| DE | 27 48 133 A1 | 5/1979 |
| EP | 1 669 459 A1 | 6/2006 |
| JP | S60-217897 A | 10/1985 |
| JP | S63-38 B2 | 1/1988 |
| WO | 98/15518 A2 | 4/1998 |
| WO | 00/17378 A2 | 3/2000 |
| WO | 2009/153886 A1 | 12/2009 |
| WO | 2011/082378 A2 | 7/2011 |

OTHER PUBLICATIONS

Dong Won Kim et al. (Ion Exchange Behavior of Alkali and Alkaline Earth Metal Ions with a Sulfonated Polystyrene and a Novel Trlazacrown Cation Exchanger, Bull. Korean Chem. Soc. 1993, vol. 16, No. 8 716-720.*
DE133 translated 1979.*
Dunuwila et al. U.S. Appl. No. 61/471,930.*
Dong Won Kim et al. (Ion Exchange Behavior of Alkali and Alkaline Earth Metal Ions with a Sulfonated Plystyrene and a Novel Trlazacrown Cation Exhanger, Bull. Korean Chem Soc 1993, vol. 16, No. 8 716-720.

(Continued)

Primary Examiner — Yevgeny Valenrod
Assistant Examiner — Blaine G Doletski
(74) Attorney, Agent, or Firm — Oliff PLC

(57) ABSTRACT

The invention is directed to a method for recovering carboyxlic acid from an magnesium carboxylate containing aqueous mixture, including the steps of: contacting the aqueous mixture with an acidic ion exchanger, thereby forming a carboxylic acid mixture and an ion exchanger loaded with magnesium ions; contacting the ion exchanger loaded with magnesium ions with a hydrochloric acid solution, thereby forming a magnesium chloride solution; and thermally decomposing the magnesium chloride solution at a temperature of at least 300° C., thereby forming magnesium oxide (MgO) and hydrogen chloride (HCl).

15 Claims, No Drawings

(56) References Cited

OTHER PUBLICATIONS

Aug. 21, 2013 International Search Report issued in International Application No. PCT/EP2013/060594.
Aug. 21, 2013 Written Opinion of the International Searching Authority issued in International Application No. PCT/EP2013/060594.

* cited by examiner

CARBOXYLIC ACID RECOVERY FROM MAGNESIUM CARBOXYLATE MIXTURE

This is a continuation of application Ser. No. 14/402,441 filed Nov. 20, 2014, which is a National Stage Application of PCT/EP2013/060594 filed May 23, 2013, and claims the benefit of Provisional Application No. 61/651,040 filed May 24, 2012 and European Application No. 12169359.2 filed May 24, 2012. The entire disclosures of the prior applications are hereby incorporated by reference herein in their entirety.

The invention is directed to a method for recovering carboxylic acid from a magnesium carboxylate containing aqueous mixture.

Carboxylic acids, such as lactic acid, succinic acid and propionic acid, can be manufactured via fermentation of carbohydrates by micro-organisms. In such a fermentation process a carbohydrate source is typically fermented by means of a micro-organism to form a carboxylic acid. The liquid wherein the carbohydrate source is fermented is called the fermentation broth or the fermentation medium.

The formation of carboxylic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH or to maintain an optimum pH value for the micro-organisms. As a result, carboxylic acid produced in the fermentation media is typically present in the form of a carboxylate salt. Although there are micro-organisms that are to some extent resistant to acidic environments, such that fermentation can be conducted at a low pH (e.g. at a pH of 3), even in these processes at least part of the carboxylic acid is obtained as a carboxylate salt.

To recover the carboxylic acid from the fermentation broth after fermentation, downstream processing is required. In such processing, the carboxylate salt in the fermentation broth needs to be converted into carboxylic acid. Also, the carboxylic acid (or carboxylate if not yet converted) needs to be isolated from the fermentation broth. Since a fermentation broth comprises many compounds, including significant amounts of biomass (such as micro-organisms) and salt (originating from the neutralizing agent), recovering and isolating carboxylic acid can be rather complex, typically requiring multiple processing steps and leading to waste material, in particular salt waste.

WO 00/17378 is directed to the preparation of lactic acid and shows an example of such processing steps. The process comprises the steps of obtaining a calcium or magnesium lactate in a fermentation reaction, separating the broth from the biomass (1), acidifying the broth with hydrochloric acid to yield lactic acid and a concentrated solution of magnesium chloride or calcium chloride (2), concentrating the solution resulting from the acidified broth, containing lactic acid and magnesium or calcium chloride (3), separating the lactic acid from the lactic acid-containing solution by liquid-liquid extraction (4), solvent recovery (5), adsorption purification (6), concentration (7) and a thermohydrolysis step to react magnesium chloride with water to yield magnesium oxide powder and hydrochloric acid (8), hydration of the magnesium oxide by quenching, thus obtaining magnesium hydroxide which is recycled to the fermentor (10) and absorption of the HCl by water (11).

A disadvantage of the process described in WO 00/17378 is that contamination of the magnesium oxide may occur in the thermohydrolysis step. The magnesium chloride solution obtained in the extraction step typically comprises impurities, in particular impurities originating from a fermentation process, for example sugars, proteins, and salts. If such impurities are present in the magnesium chloride solution during the thermohydrolysis step, they may contaminate the magnesium oxide formed.

A further disadvantage of the process described in WO 00/17378 is that the thermohydrolysis step may result in product loss due to incineration of lactate. During extraction, small amounts of lactate salt will typically remain in the aqueous phase and end up in the magnesium chloride solution to be treated in the thermohydrolysis step. Such lactate salt is lost for recovery, because it will be incinerated under the high temperatures used in this step.

A further disadvantage of the process described in WO 00/17378 is that part of the magnesium and part of chloride ions are extracted into the organic phase. Consequently, these ions are not recycled in the thermohydrolysis step. Furthermore, these ions may eventually end up in the lactic acid solution, which will thus have be removed at a later stage, e.g. by extensive washing.

A further disadvantage of the process described in WO 00/17378 is that the lactic acid solution obtained after extraction will be contaminated with the organic solution used for extraction, even after the solvent recovery step. Such impurities need to be removed to increase the purity of the lactic acid solution.

An object of the invention is to increase the efficiency of the recycling step described in WO 00/17378, in particular by overcoming one or more of the above-mentioned disadvantages.

A more general object of the invention is to provide a method for recovering carboxylic acid with high purity from a magnesium carboxylate solution, wherein the magnesium ions are separated from the carboxylate solution and subsequently recycled in a highly efficient way.

At least one of these objects was met by providing a method for recovering carboyxlic acid from a magnesium carboxylate containing aqueous mixture, comprising the steps of contacting the aqueous mixture with an acidic ion exchanger, thereby forming a carboxylic acid mixture and an ion exchanger loaded with magnesium ions; and contacting the ion exchanger loaded with magnesium ions with hydrochloric acid (HCl solution), thereby forming a magnesium chloride solution; and thermally decomposing the magnesium chloride solution at a temperature of at least 300° C., thereby forming magnesium oxide and hydrogen chloride.

The inventors realized that by using ion exchange instead of extraction to convert the carboxylate to carboxylic acid, the magnesium ions present in the aqueous mixture can be more efficiently recycled. First, the inventors realized that a very efficient separation of magnesium salt and carboxylic acid can be achieved by using ion exchange, in particular compared to extraction. Also, the process of ion exchange was found to be less prone to contaminating the solutions compared to extraction. More importantly though, the inventors found that by regenerating the ion exchanger with hydrochloric acid, a magnesium chloride solution with high purity and essentially no carboxylate or carboxylic acid is obtained. This is advantageous with respect to the thermal decomposition step. First, no carboxylate will be lost when thermally decomposing the magnesium chloride solution. Second, essentially no contamination of magnesium oxide occurs due to the high purity of the magnesium chloride solution. Since magnesium oxide can be used as a base or precursor thereof in a possible fermentation step and hydrogen chloride can be used in the regeneration step, the method of the invention provides for a process wherein the magnesium ions present in the aqueous mixture are recycled in an efficient way.

Recovering carboxylic acid from a carboxylate containing liquid by using ion exchange is known in the art, e.g. from EP 1 669 459. However, the combination of this technique with thermohydrolysis and the advantageous effects associated with this combination are not recognized.

EP 1 660 459 describes a method for bringing a liquid containing a salt of succinic acid into contact with an H-type strongly acidic cation-exchange resin, and precipitating a crystal of succinic acid from the obtained ion-exchange-treated liquid to obtain purified succinic acid. The salt may be selected from sodium succinate, potassium succinate, magnesium succinate, calcium succinate and ammonium succinate. EP 1 660 459 does not describe that magnesium can be recycled by specifically choosing magnesium succinate as the salt and obtaining a magnesium chloride solution by regenerating the exchange resin with hydrochloride acid. EP 1 660 459 is also silent about thermohydrolysis.

The method of the invention is directed to recovering carboxylic acid from a magnesium carboxylate containing aqueous mixture.

The method of the invention is preferably a continuous process, but it may also be conducted as a batch process.

The aqueous mixture may be a suspension or a solution. However, the aqueous mixture is preferably an aqueous solution. In case the ion exchange step is conducted in an ion exchange column, the presence of solid matter is generally considered undesirable, because it may result in clogging of the column. Accordingly, preferably at least 99 wt. % of the aqueous mixture, more preferably at least 99.9 wt. % of the aqueous mixture is in liquid or dissolved form, based on the total weight of the aqueous mixture.

The aqueous mixture may, besides magnesium carboxylate, also comprise carboxylic acid, for example because it originates from a fermentation step conducted at low pH. Furthermore, the aqueous mixture may comprise impurities, in particular impurities originating from a fermentation process. Such impurities may be soluble or insoluble in the aqueous mixture. Examples of dissolved impurities are sugars, proteins, and salts. Insoluble biomass (e.g. microorganisms) and insoluble salts are examples of insoluble impurities. These impurities may all be typically present in a fermentation medium.

The aqueous mixture typically originates from a fermentation process. Accordingly, the method of the invention may further comprise a fermentation step to form the carboxylate, which fermentation process comprises the steps of fermenting a carbohydrate source by means of a microorganism in a fermentation broth to form the carboxylic acid and neutralizing at least part of the carboxylic acid by addition of a magnesium base, thereby obtaining a fermentation medium comprising carboxylate salt. The fermentation medium may be used as the aqueous mixture in the method of the invention. However, solid matter (e.g. biomass or insoluble sugars such as oligosaccharides) is preferably removed from the fermentation medium prior to the ion exchange step. Any means suitable for separating solid matter from the fermentation broth can be used. For example, separation may be conducted by filtration, centrifugation and/or flocculation. Separation may be conducted by filtration of the fermentation medium obtained in the fermentation process. Microfiltration may be conducted to remove small solid particles present in the fermentation medium.

The magnesium carboxylate present in the aqueous mixture can in principle be a magnesium salt of any carboxylic acid, but in particular of a carboxylic acid that can be prepared in a fermentation process. The magnesium carboxylate may for example be a magnesium salt of a mono-, di- or tri-carboxylic acid comprising at least 2 to 8 carbon atoms (C2-C8 carboxylate). However, the present invention is also suited for longer carboxylates with more than 8 carbon atoms. In case the magnesium carboxylate is a C2-C8 carboxylates, the carboxylate may be selected from the group consisting of lactate, succinate, propionate, 3-hydroxypropionate, hydroxybutyrate, citrate, fumarate, itaconate, adipate, acrylate, levulinate, maleate, terephtalate and 2,5-furandicarboxylate. Good results have been obtained by using magnesium lactate or magnesium succinate. However, the magnesium carboxylate may also be a magnesium carboxylate other than magnesium lactate.

Magnesium salts of higher carboxylic acid that also may very well be used in the method according to the present invention can be for example the magnesium salts of a fatty acid (fatty acylate) and/or the magnesium salts of a mono- and/or di-lactylate (a lactylate ester of a fatty acid). Said magnesium fatty acids salts and lactylate salts may be selected from the magnesium salt of a fatty acid or lactylate ester of caproic, caprylic, capric, lauric, myristic, palmitic, stearic and oleic acid and/or mixtures hereof.

The content of magnesium carboxylate present in the aqueous mixture is preferably as high as possible. For example, the aqueous mixture may comprise at least 5 wt. %, preferably at least 10 wt. %, more preferably at least 15 wt. % magnesium carboxylate, even more preferably at least 20 wt. %, based on the total weight of the aqueous mixture. The aqueous mixture may be saturated with the magnesium carboxylate. However, the concentration of magnesium carboxylate is preferably not so high that precipitation of magnesium carboxylate occurs. Accordingly, the magnesium carboxylate content in the aqueous mixture is preferably lower than the solubility of the magnesium carboxylate in the aqueous mixture. The term "solubility" as used herein refers to the maximum weight amount of a compound (in this case magnesium carboxylate) that can be dissolved in a certain amount of an aqueous mixture at a certain temperature. Preferably, the aqueous mixture has a magnesium carboxylate concentration that is within 10 wt. %, more preferably within 5 wt. % of the solubility of the compound in the aqueous mixture.

Furthermore, the content of magnesium carboxylate present in the aqueous mixture is preferably chosen such that no or essentially no carboxylic acid will precipitate when the aqueous mixture is contacted with the acidic ion exchanger (ion exchange step). Precipitation of carboxylic acid during the ion exchange step may be undesirable, because it can clog the equipment used in this step, such as in the case of a column and/or a packed or fluidized bed. The skilled person will know how to determine the maximum concentration of magnesium carboxylate at which no precipitation will occur in the ion exchange step or precipitation occurs to an acceptable extent.

The method of the invention comprises the step of contacting the aqueous mixture with an acidic ion exchanger, thereby forming a carboxylic acid solution mixture (also referred to as the product mixture) and an ion exchanger loaded with magnesium ions (also referred to as the loaded ion exchanger). This step may also be referred to as the ion exchange step. In this step, the ion exchanger binds the magnesium ions and protonates the carboxylate. Thus, the ion exchange step effectively separates the carboxylate from the magnesium and protonates the carboxylate in one single step.

The acidic ion exchanger should be suitable to exchange $H^+$ for magnesium cations. The ion exchanger is thus cationic. For an efficient protonation of the carboxylate, the $pK_a$ of the ion exchanger is preferably lower than that of the protonated carboxylate (i.e. of the carboxylic acid formed after receiving the $H^+$ from the ion exchanger). The acidic ion exchanger is preferably a strongly acidic ion exchanger, because such an ion exchanger typically has a sufficiently low $pK_a$ to efficiently protonate most carboxylates. Strongly acidic ion exchanger typically comprises one or more sulphonic acid and/or phosphonic acid groups. Such groups provide the ion exchanger with a sufficiently low $pK_a$.

The acidic ion exchanger can be a solid or a liquid acidic ion exchanger.

An advantage of a solid ion exchanger is that it does not contaminate the aqueous mixture, because it does not dissolve in the aqueous mixture. Also, the ion exchanger can easily be separated from the aqueous mixture. In particular, no separate step of separating the ion exchanger from the aqueous mixture is needed. When using solid ion exchangers, the ion exchange step can be suitably conducted in a column or in a fluidized bed.

The acidic ion exchanger can be an organic ion exchanger (e.g. a polymeric ion exchange resin) or an inorganic ion exchanger (e.g. a functionalized inorganic ion exchanger). The acidic ion exchanger can further be a solid or a liquid acidic ion exchanger.

A solid acidic ion exchanger is preferably in the form of beads which may have a diameter of 0.5-2 mm. Beads are the standardized form of solid polymeric ion exchange resin and can be suitably used in ion exchanger columns, fluidized beds and SMBs.

Preferably, the acidic ion exchanger is a polymeric ion exchange resin. The polymeric ion exchange resin is preferably strongly acidic and typically comprises a polymer functionalized with one or more acid groups such as one or more sulphonic acid and/or phosphonic acid groups. Suitable polymers are those that are sufficiently stable under acidic conditions and are known to the skilled person. The polymer may be capable of forming crosslinks, which provides the polymer with a low solubility in water and/or a high melting point. Examples of suitable polymeric ion exchange resins are acid functionalized styrene-divinylbenzene or acid functionalized crosslinked polystyrene.

Functionalized inorganic ion exchangers may also be used as the solid acidic ion exchanger. However, due to their tendency to dissolve under strongly acidic conditions, the use of such ion exchangers may not be desirable in certain applications. Examples of suitable inorganic ion exchangers are functionalized silicas.

When conducting the ion exchange step in a column, the column may be packed with the ion exchanger beads described above. Such a column is known in the art and is called an ion exchange column. The aqueous mixture is typically contacted with the acidic ion exchanger by passing the aqueous mixture through the column. The aqueous mixture may be fed at the top of the column, such that gravity forces the aqueous mixture through the column. The magnesium present in the aqueous mixture binds to the resin (thus forming the loaded ion exchanger) and will remain in the column, while the carboxylate is protonated to form carboxylic acid, which acid together with the remainder of the aqueous mixture flows through and exits the column, thus forming the carboxylic acid mixture. This results in an immediate and efficient separation of the magnesium from the aqueous mixture.

When conducting the ion exchange step in a fluidized bed, the bed typically comprises the ion exchanger beads described above. The aqueous mixture is contacted with the acidic ion exchanger by passing the aqueous mixture through the fluidized bed. The bed is placed under conditions such that the aqueous mixture comprising the solid beads behaves as a fluid. As a result, solid material present in the aqueous mixture is allowed to pass through the bed. Thus, clogging of the bed can be avoided and contamination of the bed is reduced. The magnesium ions are bound to the resin beads and the carboxylic acid mixture is formed in the same way as described above for the ion exchange column. In another embodiment, the ion exchange step is conducted in a Simulated Moving Bed (SMB). The advantage of SMB is that a countercurrent flow between the solid ion exchanger and the aqueous mixture are created, which may lead to a more efficient ion exchange. The techniques of using fluidized beds and SMB are generally known and the skilled person will know how to prepare such beds, e.g. using the above-described beads.

Although the ion exchange column and the fluidized bed described above can be used to filter off solid matter, it is preferred to use an aqueous mixture that comprises essentially no solid matter, as to prevent clogging of the column or bed. Accordingly, solid matter may be removed from the aqueous mixture prior to the ion exchange step, for example by filtration. Microfiltration or ultrafiltration may be used to remove particularly small solid particles.

The acidic ion exchanger can also be a liquid acidic ion exchanger. An advantage of liquid ion exchangers is that they are very suitable for processing slurries. Since contacting the liquid ion exchangers can be efficiently conducted without the need for any equipment that can be easily clogged, the presence of solid matter does generally not pose any problems. A further advantage of a liquid ion exchanger is that it is easy to handle. Because a liquid ion exchanger can be part of a liquid stream, the process can make use of liquid streams which can be pumped around if necessary. This provides for a more flexible process.

In case a liquid ion exchanger is used, the ion exchanger is typically an organic compound that typically comprises one or more sulphonic acid and/or phosphonic acid groups. The structure thus similarities with the polymeric ionic exchange resins, but the organic compound used as a liquid ion exchanger is typically not a polymer and is not capable of forming crosslinks. The organic compound may comprise 14 or more carbon atoms, but equal or less than 40 carbon atoms (C14-40 organic compound). Organic compounds with more than 40 carbon atoms may not dissolve sufficiently in water to be effective. Organic compounds with less than 14 carbon atoms may have a too high solubility in water, which is undesirable with respect to separating the liquid ion exchanger from the carboxylic acid after the ion exchange step. Preferably, the organic compound comprises a carbon chain substituted with a sulphonated and/or phosphonated benzyl group. The compound can for example be selected from the group consisting of dinonyl naphthalene sulfonic acid (DNNSA), didodecyl napthalene sulfonic acid (DDNSA), di(2-ethylhexyl)phosphoric acid (D2EHPA), bis (2,4,4-trialkyl)phosphinic acid and bis(2,4,4-trialkyl)dithiophosphinic acid (both phosphinic acids are available from Cytec under the brand name CYANEX), such as bis(2,4,4-trimethylpentyl)phosphinic acid (active compound of CYA- NEX272) and bis(2,4,4-trimethylpentyl)dithiophosphinic acid (active compound of CYANEX301).

Liquid ion exchangers are designed to have a very low solubility in water. They typically have a solubility in water of less than 5 ppm. This has the advantage that essentially no contamination of the aqueous mixture with liquid ion exchanger will occur when these are contacted in the ion exchange step. This is in contrast with organic solvents used in regular extraction techniques, which solvent are relatively polar compared to liquid ion exchangers and will therefore partly dissolve and contaminate the aqueous phase.

The liquid ion exchanger may be dissolved in a hydrophobic solvent. Such solvents are preferably essentially insoluble in water, such that they will not contaminate the aqueous mixture by partly dissolving in it. Examples of suitable hydrophobic solvents are hydrocarbons, such as alkanes, cycloalkanes and aromatic hydrocarbons. For example, hexane, heptane, pentane, cyclohexane and toluene may be used. Mixtures of hydrocarbons can also be used, such as kerosine. When a solution of a liquid ion exchanger in a hydrophobic solvent is used, the concentration of the liquid ion exchanger in the solution may be 10-70 wt. %, preferably 25-50 gew. %, based on the total weight of the solution. However, concentrations higher than 70 wt. % may also be used. An advantage of dissolving the liquid ion exchanger is that it decreases the viscosity of the ion exchanger and/or may prevent emulsification in the aqueous mixture.

The liquid ion exchanger may also be used in pure, i.e. undissolved, form. This has the advantage that the ion exchanger is not diluted by hydrophobic solvent and the concentration of ion exchange groups is thus increased.

When conducting the ion exchange step with a liquid ion exchanger, the aqueous mixture is typically contacted with a solution of an acidic ion exchanger in a hydrophobic solvent, for example by using counter-current streams. Due to the hydrophobic nature of liquid ion exchangers, the aqueous mixture is typically not miscible with the liquid ion exchanger. Thus, an organic phase and an aqueous phase may be formed. The magnesium ions present in the aqueous mixture will bind to the ion exchanger (thus forming the loaded ion exchanger), while the carboxylate is protonated by the ion exchanger to form carboxylic acid (thereby forming the aqueous carboxylic acid mixture). The liquid ion exchanger (organic phase) can be separated from the carboxylic acid mixture (aqueous phase) by decantation.

The ion exchanger may be present in a porous particle, in which it is immobilized. An advantage of the ion exchanger being immobilized in a porous particle is that the ion exchanger can easily be separated from the aqueous mixture, for example by filtration. Also, less contamination of the aqueous mixture will occur when the ion exchanger is immobilized in a porous particle. Ion exchange is in this case conducted by contacting the aqueous mixture with the porous particles comprising the immobilized liquid ion exchanger, for example in a column. The magnesium ions present in the aqueous mixture binds to the ion exchanger present in the porous particle, thereby forming the loaded ion exchanger. The carboxylate is protonated by the ion exchanger, thereby forming a carboxylic acid mixture.

Since the process of conducting ion exchange using the ion exchangers described above is generally known in the art, the skilled person will understand how to conduct such a step and which conditions to choose without undue burden.

Preferably, the ion exchange step is conducted at high temperatures. High temperatures are desirable, because they decrease the risk of precipitation of the carboxylic acid. This is particular relevant when using an ion exchange column, which may be clogged by such precipitation. Furthermore, since the solubility of compounds increases at high temperatures, such temperatures allow for working with highly concentrated carboxylate and carboxylic acid mixture. Accordingly, the ion exchange step is preferably conducted at a temperature of at least 40° C., more preferably at a temperature of at least 70° C., even more preferably a temperature of at least 100° C. If temperatures higher than 100° C. are used, the ion exchange step may be conducted under pressure to avoid substantial loss of solvent.

The ion exchange step may comprise the use of multiple ion exchangers. This is in particularly preferred when the ion exchange step is conducted continuously (as opposed to batch-wise). In this case, the carboxylic acid mixture obtained in the ion exchange step may subsequently be brought into contact with a further acidic ion exchanger, similar to the first acidic ion exchanger. Such use of a further acidic ion exchanger can be desirable to protonate any magnesium carboxylate and bind any magnesium ions still present in the solution after having been contacted with the first ion exchange. This is in particular desirable when the ion exchange is conducted using counter-current streams of the aqueous mixture and the ion exchanger, i.e. when ion exchange is conducted by contacting a stream of the aqueous mixture (feed stream) counter-currently with a stream comprising the ion exchanger (for example a liquid stream comprising the polymeric acidic ion exchange beads described above or a liquid stream comprising the porous particles comprising the liquid ion exchanger). The concentration of the magnesium carboxylate in the aqueous mixture will thus gradually decrease, while being contacted with an ion exchanger stream with a gradually increasing concentration of still protonated ion exchanger. A similar effect can be obtained by running the aqueous mixture and subsequent carboxylic acid mixture through multiple ion exchange columns.

The loaded ion exchanger may be washed, preferably with water, before contacting it with hydrochloric acid. Thus, any remaining amounts of carboxylic acid and/or carboxylate can be removed from the loaded ion exchanger. This may result in a diluted carboxylic acid mixture. Any carboxylic acid thus obtained can be added to the carboxylic acid mixture. A further advantage of this washing step is that it may increase the purity of the magnesium chloride solution. Compounds other than magnesium ions may be removed by the washing step, such that they will not end up in the magnesium chloride solution.

The carboxylic acid mixture obtained in the ion exchange step may be a carboxylic acid solution or a carboxylic acid suspension. In certain embodiments, it is preferred to use a magnesium carboxylate solution as the magnesium carboxylate containing mixture, in which case the obtained carboxylic acid mixture will also be in the form of a solution. However, in case the ion exchange step is conducted using a suspension as the aqueous mixture, the carboxylic acid mixture obtained after ion-exchange can also be a suspension. A carboxylic acid suspension may for example be formed in case the ion exchange step is conducted using a liquid ion exchanger or a fluidized bed.

In a preferred embodiment, part of the carboxylic acid mixture (product mixture) is fed back to the magnesium carboxylate containing aqueous mixture, said part is preferably a solution. This may be done during, but preferably prior to the ion exchange step. In the latter case, part of the carboxylic acid mixture is thus added to the magnesium carboxylate containing aqueous mixture. This may result in dissolving at least part (but preferably all) of any solid magnesium carboxylate present in the aqueous mixture. The inventors surprisingly found that by feeding back at least part of the product solution to the aqueous mixture, the carboxylic acid concentration in the carboxylic acid mixture obtained in the ion exchange step may be increased. Carboxylic acid concentrations above 20 wt. % can thus be obtained in the aqueous carboxylic acid mixture. It is contemplated that a carboxylic acid solution other than the product mixture may also be used to achieve the same effect (provided that the carboxylic acid in the solution corresponds to the carboxylate in the aqueous mixture). The carboxylic acid solution fed to the aqueous mixture may have a carboxylic acid concentration of 5-25 wt. %.

The carboxylic acid can be recovered from the carboxylic acid mixture by any method know in the art, for example by precipitation or water evaporation. Precipitation is in particular preferred when recovering succinic acid. Part of the carboxylic acid mixture may be fed back to the aqueous mixture. As described above, this may increase final carboxylic acid concentration in the carboxylic acid mixture.

The method of the invention further comprises the step of contacting the ion exchanger loaded with magnesium ions with hydrochloric acid, thereby forming a magnesium chloride solution. In addition, by contacting the loaded ion exchanger with hydrochloric acid, the ion exchanger is regenerated to its acidic form. Therefore, this step may also be referred to as the regeneration step.

The hydrochloric acid used is preferably a concentrated solution of hydrogen chloride in water, for example with a concentration of at least 10 wt. %, preferably at least 20 wt. % hydrogen chloride, based on the total weight of the hydrochloric acid solution. The higher the concentration of hydrochloric acid is, the more concentrated magnesium chloride solution will be obtained. A concentrated magnesium chloride solution is desirable due to the lower energy costs for thermally decomposing such a solution in the thermal decomposition step.

Since essentially no carboxylate, carboxylic acid or soluble impurities originally present in the aqueous mixture are bound by the ion exchanger, the magnesium chloride can be obtained in very pure form. This is desirable with respect to the thermal decomposition step, wherein any compounds other than magnesium chloride are lost for recovery and/or contaminate the products formed in this step, in a particular magnesium oxide.

The temperature at which the regeneration step is conducted is 20-120° C., preferably 60-100° C. On the one hand, temperatures should be sufficiently high to avoid any precipitation of magnesium chloride, in particular when using an ion exchange column. However, temperatures higher than 120° C. are generally undesirable, because they may damage the equipment and/or the ion exchanger used.

The regenerated ion exchanger may still comprise small amounts of chloride. In case such a regenerated ion exchanger would be used to perform another ion exchange step according to the method of the invention, chloride ions would contaminate the carboxylic acid mixture obtained in such an ion exchange step. Therefore, the regenerated ion exchanger is preferably washed before using it again in an ion exchange step. Accordingly, the method of the invention may comprise the step of washing the regenerated ion exchanger, in particular to remove any chloride ions. Such a washing step is typically conducted using water. Thus, contamination of the carboxylic acid mixture with chloride can be easily prevented in the method of the invention. This is an advantage over using extraction, as done by WO 00/17378, wherein it is very difficult to prevent chloride from contaminating the end product due to extraction of chloride during liquid-liquid extraction The method of the invention further comprises the step of thermally decomposing the magnesium chloride solution at a temperature of at least 300° C., thereby forming magnesium oxide and hydrogen chloride. This step may also be referred to as the thermal decomposition step.

In the thermal decomposition step, the magnesium chloride solution obtained in the regeneration step is subjected to a thermal decomposition step at temperatures of at least 300° C. Magnesium chloride ($MgCl_2$) is thermally decomposed under formation of magnesium oxide (MgO) and hydrogen chloride (HCl). As also described above, the efficiency of this recycle step very much depends on the purity of the magnesium chloride solution. In case carboxylate or carboxylic acid would be present in the magnesium chloride solution, this would result in a decrease in the final recovery yield, because the carboxylate or carboxylic acid will be incinerated under the high temperatures used in this step. Furthermore, the presence of impurities in the magnesium chloride solution would result in contamination of the products formed in the thermal decomposition step, in particular contamination of magnesium oxide. The inventors found that the magnesium chloride obtained in the method of the invention does not contain such carboxylate, carboxylic acid and impurities, such that the thermal decomposition step provides for a very efficient way of recycling the magnesium ions in the aqueous mixture.

The compounds formed in the thermal decomposition step can be recycled in other stages in the method of the invention.

The magnesium oxide may be used in a fermentation process. Magnesium oxide is a base and can thus be used in a fermentation process as a neutralizing agent or as a precursor thereof. At least part of the magnesium oxide may for this purpose be brought in contact with water to obtain a magnesium hydroxide ($Mg(OH)_2$) slurry (or a mixture of magnesium hydroxide and magnesium oxide). Magnesium oxide may also be directly added to the fermentation broth of a fermentation process. It is also possible to use mixtures of magnesium oxide and magnesium hydroxide. Accordingly, the method of the invention may further comprise the step of recycling MgO and/or $Mg(OH)_2$ for use in a fermentation process, in particular in the fermentation process wherein the carboxylate is formed. MgO and/or $Mg(OH)_2$ can be used as a neutralizing agent or precursor thereof. When used in a fermentation process, a mixture of MgO and/or $Mg(OH)_2$ may be a desirable neutralizing agent. By varying the composition of the MgO and/or $Mg(OH)_2$ mixture, the fermentation process can be optimized. The preferred composition of the mixture depends on the fermentation conditions and the type of microorganism used in the fermentation.

The hydrogen chloride is typically dissolved in water during or after thermal decomposition, thereby obtaining hydrochloric acid (HCl solution). Such a solution can be used in the regeneration step of the method of the invention. Accordingly, the method of the invention may further comprise the step of:
  dissolving the hydrogen chloride in water, thereby obtaining hydrochloric acid, which hydrochloric acid may be recycled for use in regeneration of the ion exchanger to its acidic form.

Thus, the method of the invention provides for a process wherein the salt waste, i.e. the magnesium and chloride ions) can be efficiently recycled.

The invention will be further illustrated by the following examples.

EXAMPLE 1

Ion Exchange of Magnesium Lactate to Lactic Acid on Strong Cation Exchange Resin A magnesium lactate feed solution was prepared by adding 8 g of magnesium lactate dihydrate to 92 g water and mixing to complete dissolution. The thus prepared feed solution comprised 6.8 wt % of magnesium lactate in water. The solution was heated to 20° C.

Although magnesium carboxylate solutions obtained in a fermentation process typically comprise additional compounds (in particular impurities such as sugars, protein and/or biomass), the feed solution prepared in this example is considered to sufficiently resemble such solutions for the proof of principle shown in this Example to apply to feed solutions obtained in a fermentation process as well.

50 ml of Amberlite FPC23 H resin was put in the glass column. The column was heated to 20° C. Resin was washed with 3 bed volumes of water. The water flow was then stopped and 6.8 wt % of magnesium lactate solution was pumped through the column with the flow of 0.83 ml/min. The pH of the feed solution was determined to be pH 6.2. The first product sample was taken after 50 min. The sample had a pH 2 and the magnesium content measured by atomic adsorption spectrometry below the detection limit of 5 ppm, indicating that the ion exchanger had exchanged $H^+$ ions for magnesium ions. The concentration of lactate ions remained constant at 7.1 wt %.

This example shows simultaneous removal of magnesium ions and acidulation of magnesium lactate to lactic acid by cation exchange resin, resulting in an ion exchanger loaded with magnesium ions and an aqueous lactic acid solution.

EXAMPLE 2

Formation of Magnesium Chloride Solution

The magnesium ion loaded Amberlite FPC23 H resin used in Example 1 was washed with 3 BV of water to remove any residual magnesium lactate and lactic acid.

Then 108 g of 37 wt % hydrochloric acid was mixed with 692 g of water resulting in 5 wt % hydrochloric acid solution. This solution was pumped through the column with flow of 1.7 ml/min. Every 30 min product samples were taken and pH of the sample and magnesium content was measured. After 60 min pH of the taken sample was 0.30 and magnesium content was 9070 ppm. After 90 min the product sample had a pH value of −0.15 and magnesium content of 3910 ppm.

This example shows that magnesium is recovered from strong cation exchange resin in the form of a magnesium chloride solution. The magnesium chloride solution had a high purity. No lactic acid or lactate was detected and decomposable salts that may decrease the efficiency of the thermal decomposition step were expected to be removed by the washing step.

EXAMPLE 3

Ion Exchange of Magnesium Lactate to Lactic Acid on Liquid Ion Exchanger

A magnesium lactate feed solution was prepared by adding 7.4 g of magnesium lactate dihydrate to 15.2 g water. The prepared feed solution comprised 28 wt % of magnesium lactate slurry in water. Solution was prepared at 20° C.

Although magnesium carboxylate solutions obtained in a fermentation process typically comprise additional compounds (in particular impurities such as sugars, protein and/or biomass), the feed solution prepared in this example is considered to sufficiently resemble such solutions for the proof of principle shown in this Example to apply to feed solutions obtained in a fermentation process as well.

The liquid ion exchanger was prepared by adding 25 g of dinonylnaphthalenesulfonic acid to 25 g of heptane and mixing till complete dissolution. The liquid ion exchanger thus comprised 50 wt % of dinonylnaphthalenesulfonic acid.

The liquid ion exchanger (50 g) was mixed with 22.6 g of 28 wt % magnesium lactate slurry at 20° C. and mixed for 2 hours. The thus obtained solution was transferred to a separation funnel where two phases were observed: an aqueous phase and an organic phase. Using the separation funnel, 7.8 g of aqueous phase was separated off. The aqueous phase had a pH of 1.8 and contained 17 wt % of lactic acid, indicating that the ion exchanger had exchanged $H^+$ ions for magnesium ions and that the lactic acid formed in this process was present in the aqueous phase.

Then, 10 g of fresh water was added to the organic layer in the separation funnel, after which the funnel was shaken and phases were again separated. 10.6 g of aqueous phase was separated. This aqueous phase had a pH of 1.93 and contained 7.5 wt % of lactic acid.

In this experiment, the magnesium content was decreased from 3.36 wt. % in the magnesium carboxylate solution to 2280 ppm in the aqueous phase after ion exchange.

Thus, the example shows simultaneous removal of magnesium ions and acidulation of magnesium lactate to lactic acid by a cation liquid ion exchanger.

EXAMPLE 4

Regeneration of Liquid Ion Exchanger

An amount of 20 g hydrochloric acid solution (20 wt % in water) was added to 60.6 g of the organic phase obtained after the phase separations in Example 3. The mixture was stirred for 50 min at 20° C. Afterwards, the mixture was transferred to a separation funnel. Two phases were observed: an organic layer and an aqueous layer. The aqueous layer was separated and the magnesium content was analyzed using atomic adsorption spectrometry. The layer comprised 8100 ppm of magnesium, indicating that an aqueous magnesium chloride solution was formed.

This example shows that magnesium can be recovered from liquid ion exchanger in the form of a magnesium chloride solution by exchanging hydrogen ions present in hydrochloric acid with magnesium ions present in the cation liquid exchanger.

EXAMPLE 5

Ion Exchange of Magnesium Succinate to Succinic Acid Using a Strong Cation Exchange Resin A magnesium succinate feed solution was prepared by adding 151.3 g of magnesium succinate tetra hydrate to 848.7 g water and mixing to complete dissolution. The thus prepared feed solution comprised 10 wt % of magnesium succinate in water. The solution was heated to 60° C.

Although magnesium carboxylate solutions obtained in a fermentation process typically comprise additional compounds (in particular impurities such as sugars, protein and/or biomass), the feed solution prepared in this example is considered to sufficiently resemble such solutions for the proof of principle shown in this Example to apply to feed solutions obtained in a fermentation process as well.

A glass column of 100 ml was filled with beads of a strongly acidic cation exchange resin comprising sulfonate groups (available under the name Amberlite FPC23 H). The column was heated to 60° C. The resin was washed with 3 bed volumes (BV) of water. The water flow was then stopped and 10 wt % of magnesium succinate solution was pumped through the column with a flow of 3.5 ml/min. The pH of the feed solution was determined to be pH 7. Every 20 minutes, a product sample was taken and its pH value was measured. Also, its magnesium content was measured by atomic adsorption spectrometry. The product sample taken after 20 min had a pH value of 2.2 and a magnesium content below the detection limit of 5 ppm, indicating that the ion exchanger had exchanged $H^+$ ions for magnesium ions. The concentration of succinate remained constant at 8.2 wt %.

This example thus shows simultaneous removal of magnesium ions and acidulation of magnesium succinate to succinic acid by an acidic cation exchange resin, resulting in an ion exchanger loaded with magnesium ions and an aqueous succinic acid solution.

EXAMPLE 6

Formation of Magnesium Chloride Solution

The magnesium ion loaded Amberlite FPC23 H resin used in Example 5 was washed with 3 bed volumes (BV), corresponding to 100 ml of water, to remove any residual magnesium succinate and succinic acid, as well as any decomposable salts (such as NaCl, KCl and $CaCl_2$) if present.

Then 108 g of 37 wt % hydrochloric acid was mixed with 692 g of water resulting in 5 wt % hydrochloric acid solution. This solution was pumped through the column with flow of 3.5 ml/min. Every 20 min product sample was taken, pH value of the sample and magnesium content was measured. After 20 min pH of the product sample was 6.8 and magnesium content was 4600 ppm. After 40 min the product sample had a pH of 0.38 and magnesium content of 12300 ppm. No succinic acid or succinate could be detected in the samples (detection limit<0.1 wt. %).

This example shows that magnesium is recovered from strong cation exchange resin in the form of a magnesium chloride solution. The magnesium chloride solution had a high purity. No succinic acid or succinate was detected and decomposable salts that may decrease the efficiency of the thermal decomposition step were expected to be removed by the washing step.

The invention claimed is:

1. A method for recovering carboyxlic acid, comprising the steps of
fermenting a carbohydrate source by means of a microorganism in a fermentation broth to form a carboxylic acid and neutralising at least part of the carboxylic acid by addition of a magnesium base thereby forming a fermentation medium comprising a magnesium carboxylate salt,
subjecting the fermentation medium to a step wherein solid matter is removed to form an aqueous mixture,
contacting the aqueous mixture with an acidic ion exchanger, thereby forming a carboxylic acid mixture and an ion exchanger loaded with magnesium ions; and
contacting the ion exchanger loaded with magnesium ions with a hydrochloric acid solution, thereby forming a magnesium chloride solution; and
thermally decomposing the magnesium chloride solution at a temperature of at least 300° C., thereby forming magnesium oxide (MgO) and hydrogen chloride (HCl).

2. The method according to claim 1, further comprising dissolving the HCl in water, thereby obtaining a HCl solution; and
bringing the MgO in contact with water, thereby obtaining $Mg(OH)_2$.

3. The method according to claim 2, wherein the HCl solution is recycled for use in contacting the ion exchanger loaded with magnesium ions.

4. The method according to claim 1, wherein MgO and/or $Mg(OH)_2$ is recycled for use in a fermentation process.

5. The method according to claim 1, wherein at least part of the carboxylic acid mixture is fed back to the aqueous mixture.

6. The method according to claim 1, wherein the ion exchanger loaded with magnesium ions is washed with water before contacting it with the hydrochloric acid solution.

7. The method according to claim 1, wherein the acidic ion exchanger is strongly acidic and comprises one or more sulphonic acid and/or phosphonic acid groups.

8. The method according to claim 1, wherein the acidic ion exchanger is a solid acidic ion exchanger.

9. The method according to claim 1, wherein the ion exchange step is conducted in an ion exchange column.

10. The method according to claim 1, wherein the ion exchange step is conducted in a fluidized bed or a simulated moving bed of polymeric ion exchange resin beads.

11. The method according to claim 1, wherein the acidic ion exchanger is a liquid acidic ion exchanger.

12. The method according to claim 11, wherein the acidic ion exchanger is an organic compound comprising one or more sulphonic acid and/or phosphonic acid groups, wherein the acidic ion exchanger is optionally dissolved in a hydrophobic solvent.

13. The method according to claim 1, wherein the carboxylic acid is selected from the group consisting of lactic acid, succinic acid, propionic acid, 3-hydroxypropionic acid, hydroxybutyric acid, citric acid, fumaric acid, itaconic acid, adipic acid, acrylic acid, levulinic acid, maleic acid, terephthalic acid, 2,5-furandicarboxylic acid, lactylic acids and fatty acids.

14. The method according to claim 1, wherein at least 99 wt. % of the aqueous mixture is in liquid or dissolved form, based on the total weight of the aqueous mixture.

15. The method according to claim 1, wherein contacting the aqueous mixture with the acidic cation exchanger is conducted at a temperature of at least 40° C.

* * * * *